United States Patent [19]
Offermanns et al.

[11] 4,084,057
[45] Apr. 11, 1978

[54] PROCESS FOR THE PRODUCTION OF 4-ACYLAMIDO-4, 4-DICARBALKOXY-BUTANALPHENYLHYDRAZONE

[75] Inventors: Herbert Offermanns; Horst Weigel, both of Hanau, Germany

[73] Assignee: Deutsche Gold- und Silber-Scheideanstalt vormals Roessler, Frankfurt, Germany

[21] Appl. No.: 819,406

[22] Filed: Jul. 26, 1977

[30] Foreign Application Priority Data

Oct. 20, 1976 Germany .............................. 2647255

[51] Int. Cl.² ............................................ C07C 101/26
[52] U.S. Cl. ...................................... 560/34; 548/309; 260/326.14 T
[58] Field of Search .......................................... 560/34
[56] References Cited

U.S. PATENT DOCUMENTS

| | | | |
|---|---|---|---|
| 2,583,010 | 1/1952 | Opie et al. .................. | 260/326.14 T |
| 3,019,232 | 1/1962 | Sakurai et al. ...................... | 548/309 |
| 4,001,276 | 1/1977 | Tsuchihashi et al. ....... | 260/326.14 T |

FOREIGN PATENT DOCUMENTS

| | | | |
|---|---|---|---|
| 619,472 | 5/1961 | Canada .......................... | 260/326.14 T |
| 2,134,360 | 12/1975 | Germany .............................. | 560/34 |

OTHER PUBLICATIONS

Moe et al., J. Amer. Chem. Soc., 70, pp. 2763-2765, (1948).
Chibata et al., Chem. Absts., 51, 11451(e), (1957).
Kalnins et al., Chem. Absts., 85, 123349(h), (1976).

*Primary Examiner*—James O. Thomas, Jr.
*Assistant Examiner*—G. T. Breitenstein
*Attorney, Agent, or Firm*—Cushman, Darby & Cushman

[57] ABSTRACT

There is provided a process for the production of 4-acylamido-4,4-dicarbalkoxy-butanalphenylhydrazones comrising adding an acylamidomalonic acid ester to acrolein in the presence of a catalyst and then reacting the 4-acylamido-4,4-dicarbalkoxy-butanal with phenylhydrazine. The catalyst is an alkali metal salt of a carboxylic acid.

13 Claims, No Drawings

PROCESS FOR THE PRODUCTION OF 4-ACYLAMIDO-4,4-DICARBALKOXY-BUTANALPHENYLHYDRAZONE

BACKGROUND OF THE INVENTION

The object of the invention is a process for the production of 4-acylamido-4,4-dicarbalkoxy-butanalphenylhydrazone by addition of an acylamidomalonic acid ester to acrolein in the presence of a catalyst and subsequent reaction of the 4-acylamido-4,4-dicarbalkoxybutanal with phenylhydrazine.

There are already known numerous processes for the production of 4-acylamido-4,4-dicarbalkoxybutanalphenylhydrazone, an important intermediate product in the synthesis of tryptophane by the Warner and Moe technique. They are differentiated essentially by the conditions in the Michael addition of the acylamidomalonic acid ester to acrolein:

In Moe et al., J. Amer. Chem. Soc. 70 (1948), 2763–2765 there is described the Michael addition in the presence of sodium alcoholates. In the most favorable cases, use of benzene as the solvent and sodium methylate as the catalyst, the yield of phenylhydrazone is 87%.

In the Bull. Agr. Chem. Soc. Japan 21 (1957), 58 et seq. (cited in C.A. 51, 11451d), there is described the Michael addition in the presence of sodium methylate, sodium hydroxide, potassium hydroxide, potassium carbonate, sodium cyanide, barium hydroxide, di and triethylamine or basic ion exchange resins. The yields of phenylhydrazone amount to 60 to 77%.

In Novotny German Auslegeschrift 21 34 360 there is described the carrying out of the Michael addition in aqueous suspension in neutral or slightly alkaline suspension, the working example being carried out using sodium hydroxide. The yield of phenylhydrazone is stated to be quantitative, but there is formed a highly impure product.

SUMMARY OF THE INVENTION

The process of the invention is characterized by the addition of the acylamidomalonic acid ester taking place in the presence of at least one alkali salt of a carboxylic acid as catalyst.

In contrast to the strongly basic catalysts used in the known processes the alkali salts of carboxylic acids are not typical catalysts for the Michael addition. Although they are not able to catalyze the addition of acylamidomalonic acid esters to acrylonitrile or an acrylic acid ester, surprisingly their presence effects a high reaction with the addition to acrolein. A further substantial advantage of the catalysts used in the process of the invention is their lower basicity in comparison with typical known catalysts for the Michael addition. As a result undesired side reactions of the acrolein are largely avoided and the 4-acylamido-4,4-dicarbalkoxy-butanal or its phenylhydrazone accrue in higher purity.

There are especially suited as catalysts for the process of the invention alkali salts of carboxylic acids having 2 to 8 carbon atoms, e.g., hydrocarbon substituted carboxylic acids, e.g., alkanoic acids and aryl carboxylic acids, for example the lithium, sodium and/or potassium salts of saturated fatty acids such as acetic acid, propionic acid, butyric acid, valeric acid, caproic acid, heptylic acid or caprylic acid, or benzoic acid. Especially preferred are sodium and/or potassium acetate. However, there can be used any of the salts of such carboxylic acids, e.g., lithium acetate, sodium propionate, potassium propionate, sodium butyrate, lithium butyrate, potassium butyrate, sodium valerate, potassium valerate, sodium caproate, potassium caproate, sodium heptylate, sodium caprylate, potassium caprylate, sodium benzoate, potassium benzoate, lithium benzoate and sodium 4-methylbenzoate. The catalysts can be employed individually or as mixtures. In order to produce an adequate reaction velocity it is suitable to use the catalysts in an amount of at least about 3 grams per mole of acylamidomalonic acid ester. An increase in the amount of catalyst above about 20 grams per mole of acylamidomalonic acid ester imparts scarcely any recognizable advantage and consequently is likely to be uneconomical. As acylamidomalonic acid ester there is preferably used diethyl acitamidomalonate. Other acylamidomalonic acid esters which can be used include the di lower alkyl esters, e.g., where the alkyl has 1 to 5 carbon atoms such as dimethyl acetamidomalonate, dipropyl acetamidomalonate, dibutyl acetamidomalonate, diamyl acetamidomalonate, diethyl propionamidomalonate, diethyl butyramidomalonate and diethyl valeramidomalonate.

The addition of the acrolein is advantageously carried out in an alcohol or a mixture of an alcohol and water wherein methanol or ethanol or a mixture of methanol and water or ethanol and water or a mixture of both methanol and ethanol with water. Other alcohols which can be employed alone or mixed with water include for example isopropyl alcohol and n-propanol. The ratio of alcohol to water is not critical and can be varied widely. For example, the mixture of alcohol and water can be from 10 to 99% alcohol by weight.

Insofar as the catalysts used are only difficultly soluble in the solvent employed they are suitably added as a solution in water. If one is content with an increased reaction time the Michael addition can also be carried out in aqueous suspension.

The exothermic addition reaction is suitably carried out at temperatures between +5° and 40° C, preferably at 10° to 25° C.

The 4-acylamido-4,4-dicarbalkoxy-butanal formed in the Michael addition is reacted in conventional manner, e.g., in weakly acid, for example acetic acid solution, with phenylhydrazine. The reaction of phenylhydrazine with aldehydes to form phenylhydrazones of course is a classic reaction and the exact procedure is not critical. The phenylhydrazone formed in the invention can be isolated in conventional manner, e.g., filtration. However, it can also be cyclized with aqueous sulfuric acid to skatylacylamidomalonic acid ester, the next step of the tryptophane synthesis according to Warner and Moe, without prior isolation.

Unless otherwise indicated all parts and percentages are by weight.

The process can comprise, consist essentially of or consist of the steps set forth with the materials recited. The invention will be explained further by the following examples.

DESCRIPTION OF THE PREFERRED EMBODIMENTS

EXAMPLE 1

There were present in a flask equipped with a stirrer, inlet, thermometer and reflux condenser 0.5 mole (108.6 grams) of diethyl acetamidomalonate (acetamidomalonic acid diethyl ester), 10 grams of sodium acetate (NaAc . 3H$_2$O) and 190 ml of methanol. 0.525 mole (29.4 grams) of acrolein were stirred in within 45 minutes while the temperature was held at 15° to 25° C by occasional cooling. There was a post reaction time of 75 minutes for the clear, colorless solution at about 20° C. After addition of 25 ml of glacial acetic acid and 0.525 mole (56.8 grams) of phenylhydrazine the temperature increased to about 35° C. After 10 to 20 minutes the mixture was heated to boiling under reflux for 1 hour. After cooling to 15° C the product was filtered off with suction and first washed with a little cold methanol and then with water and dried. The yield of colorless, pure 4-acetamido-4,4-dicarbethoxy-butanalphenylhydrazone was 176.5 grams, corresponding to a yield of 97.2% of theory. Melting Point: 138°–139° C.

EXAMPLE 2

There were present in a flask equipped with a stirrer, inlet, thermometer and reflux condenser 0.5 mole (108.6 grams) of diethyl acetamidomalonate, 8 grams of potassium acetate and 200 ml of 70% aqueous methyl alcohol. 0.525 mole (29.4 grams) of acrolein were stirred in in three portions within 30 minutes. The reaction temperature was held between 10° and 25° C. There was a post reaction time of 75 minutes at 20° C. The reaction with phenylhydrazine and the isolation were carried out as in Example 1. The yield was 174.9 grams of colorless product, corresponding to 96.3% of theory. Melting Point: 137° C.

EXAMPLE 3

There were present in a vessel equipped with a stirrer 0.25 mole (54.3 grams) of diethyl acetamidomalonate, 5 grams of sodium acetate (dissolved in 5 ml of water) and 100 ml of ethyl alcohol. There were stirred in within one hour 0.255 mole (14.3 grams) of acrolein while the temperature was held at 15° to 25° C. 75 minutes of post reaction was at about 20° C. There were poured into the colorless solution 12 ml of glacial acetic acid and 0.25 mole (27.0 grams) of phenylhydrazine and after 20 minutes the mixture was heated to 75° C for 1 hour. The phenylhydrazone formed was worked up further without isolation and cyclized by heating with aqueous sulfuric acid. Initially thereby ethyl alcohol distilled off, then boiling was under reflux.

The yield of light brown skatylacetamidomalonic acid ester was 76.8 grams, corresponding to 88.7% of theory. Melting Point: 151°–153° C.

EXAMPLE 4

There were present in a flask equipped with a stirrer, inlet, thermometer and reflux condenser 0.5 mole (108.6 grams) of diethyl acetamidomalonate, 2 grams of sodium n-butyrate and 200 ml of methanol. 0.525 mole (29.4 grams) of acrolein were stirred in within 45 minutes. The temperature was held between 20° and 25° C. Post reaction time was 2 hours at 25° C.

The reaction with phenylhydrazine and the isolation were carried out as in Example 1.

The yield of colorless phenylhydrazone was 176 grams, corresponding to 96.9% of theory. Melting Point: 138°–139° C.

EXAMPLE 5

There were present in a flask equipped with stirrer, inlet, thermometer and relux condenser 0.5 mole (108.6 grams) of diethyl acetamidomalonate, 7.5 grams of lithium benzoate and 200 ml of methanol. 0.525 mole (29.4 grams) of acrolein were stirred in in three portions while the temperature was held at 15° to 25° C. Post reaction time was 1 hour at 20° C.

The reaction with phenylhydrazine and the isolation were carried out as in Example 1.

The yield of colorless phenylhydrazone was 173.2 grams, corresponding to 95.4% of theory. Melting Point: 137°–138° C.

What is claimed is:

1. In a process for the production of 4-acylamido-4,4-dicarbalkoxy-butanalphenylhydrazone by addition reaction of an acylamidomalonic acid ester with acrolein in the presence of a catalyst and subsequent reaction of the 4-acylamido-4,4-dicarbalkoxy-butanal with phenylhydrazine the improvement comprising using as the catalyst in the addition of the acylamidomalonic acid ester with acrolein an alkali metal salt of an alkanoic acid or aromatic hydrocarbon carboxylic acid having 2 to 8 carbon atoms.

2. The process of claim 1 wherein the acylamido group is an alkanoylamido having 2 to 5 carbon atoms.

3. The process of claim 2 wherein the dicarbalkoxy group has 1 to 5 carbon atoms in each alkoxy.

4. The process of claim 3 wherein the catalyst has 2 to 7 carbon atoms.

5. The process of claim 1 wherein the catalyst is a sodium, potassium or lithium salt of an (1) alkanoic acid having 2 to 8 carbon atoms or (2) benzoic acid.

6. The process of claim 5 wherein the acylamido compound employed is diethyl acetamidomalonate.

7. The process of claim 6 wherein the catalyst has 2 to 7 carbon atoms.

8. The process of claim 7 wherein the catalyst is sodium acetate or potassium acetate.

9. The process of claim 8 wherein the catalyst is used in an amount between 3 and 20 grams per mole of diethylacetamidomalonate.

10. The process of claim 1 wherein the catalyst is employed in an amount of at least 3 grams per mole of acylamidomalonate.

11. The process of claim 10 wherein the catalyst is employed in an amount of 3 to 20 grams per mole of acylamidomalonate.

12. The process of claim 11 wherein the acylamidomalonate is a di lower alkyl acetamidomalonate.

13. The process of claim 11 wherein the reaction of the acrolein and acylamidomalonate is carried out in a lower alkanol, water or mixture of lower alkanol and water.